United States Patent [19]

Yolken

[11] Patent Number: 4,713,328

[45] Date of Patent: Dec. 15, 1987

[54] MICROBIAL ENZYME ASSAYS

[76] Inventor: Robert H. Yolken, 9120 Gorman Rd., Laurel, Md. 20810

[21] Appl. No.: 567,152

[22] Filed: Jan. 3, 1984

Related U.S. Application Data

[63] Continuation of Ser. No. 307,323, Sep. 30, 1981, abandoned.

[51] Int. Cl.$^4$ .......................... C12Q 1/34; C12Q 1/04; C12Q 1/06; C12Q 1/02
[52] U.S. Cl. ........................................ 435/18; 435/29; 435/35; 435/39; 435/803; 435/810
[58] Field of Search .................. 435/4, 18, 29, 32, 34, 435/39, 35, 803, 810; 436/68; 424/1

[56] References Cited

U.S. PATENT DOCUMENTS

| | | |
|---|---|---|
| 3,644,177 | 2/1972 | Zyk . |
| 3,830,700 | 8/1974 | O'Callaghan et al. . |
| 3,957,584 | 5/1976 | Kronish et al. ........................ 435/18 |
| 3,969,496 | 7/1976 | Schrot . |
| 4,057,470 | 11/1977 | Schrot ................................ 435/289 |
| 4,104,126 | 8/1978 | Young . |
| 4,234,683 | 11/1980 | McMillian ............................. 435/18 |
| 4,242,447 | 12/1980 | Findl et al. ............................ 435/18 |

OTHER PUBLICATIONS

Yolken, et al, Rapid Diagnosis of Infections Caused by Beta-Lactamase Producing Bacteria by Means of an Enzyme Radioisotopic Assay, J. of Ped., *Chem Abst*, vol. 94, p. 148, 1425v.
Kono, et al, Nuclear Magnetic Resonance Spectometer assay of Beta-Lactamase, *Chem Abst*, vol. 92, 1980, pp. 256-257, 123840.
Yolken et al, J. Pediatrics, 97(5):715-720, Nov. 1980.
Harris et al, Proc. Nat'l. Acad Sci., USA, 76(10):5336-5339, (1979).
Schindler et al, Chemical Abstracts, 94:169966w, p. 288, (1981).
Hash, *Methods in Enzymology*, vol. XLIII, Antibiotics, Academic Press, San Francisco, 69–85 and 263–273, (1975).

*Primary Examiner*—Esther M. Kepplinger
*Attorney, Agent, or Firm*—Holman & Stern

[57] ABSTRACT

A method is disclosed for efficient, rapid diagnosis of bacterial infections by measuring for the presence of beta-lactamase using $^{14}$C-benzylpenicillin as an enzyme substrate and isolating cleaved substrate with an ion exchange column.

22 Claims, No Drawings

MICROBIAL ENZYME ASSAYS

This is a continuation of application Ser. No. 307,323, filed Sept. 30, 1981 abandoned.

BACKGROUND OF THE INVENTION

1. Field of the Invention

This invention relates to assays for detecting microbial infections in mammals by the detection of the action of enzymes produced by the microbes upon suitable substrates.

2. Description of the Background Art

The successful treatment of an infectious disease requires its prompt recognition and diagnosis. Currently, specific therapy of infectious diseases is largely limited to infections caused by bacteria and fungi. It is thus most important that bacterial or fungal infections be promptly recognized. Rapid diagnosis is especially important in newborns, immunocompromised children and patients undergoing cancer treatment in whom the rapid institution of appropriate chemotherapy is necessary to prevent a high rate of morbidity and mortality. However, currently available cultivation techniques are often not sufficiently rapid so that the diagnostic information is available to the physician at a time when a therapeutic decision must be made. This is especially true in the case of systemic fungal infections, which are often not diagnosed by cultivation techniques until long after the start of the clinical illness. While antigen detection systems such as counter-immunoelectrophoresis, radioimmunoassay and enzyme-linked immunosorbent assay can provide for rapid diagnosis of certain cases, they are limited to the detection of a single or small number of antigens. Immunological assays are not practical for the detection of antigens which have multiple antigenic types. Such assays are thus not useful for the diagnosis of febrile patients who might have an infection caused by any one of a large number of microorganisms. While microscopic techniques such as gram staining can provide valuable information in a short period of time, the sensitivity and scope of these techniques are limited and their results are subject to observer error. Also, available assays for bacterial endotoxins are not sufficiently sensitive to provide for a reliable diagnosis of systemic bacterial infection. In addition, currently available radiometric assays, which measure the generation of $^{14}CO_2$ from $^{14}C$-glucose, require 16 to 24 hours to complete and often exhibit non-specific reactions since they measure a metabolic pathway common to both microbial and human cells. This is especially a problem in the testing of blood specimens from newborns and infants, where the increased metabolism of white cells makes the results of such assay systems difficult to interpret. In addition, these systems do not have the ability to detect fungal infections.

SUMMARY OF THE INVENTION

A more efficient approach to the detection of microbial infection in body fluids than that of the background art would be the measurement of a reaction pathway which occurs in a wide variety of microorganisms but which does not occur in human cells. For example, bacteria and fungi possess a number of enzymes not produced by mammalian cells, and the detection of one of these unique microbial enzymes in the blood or body fluid of a human might thus indicate microbial infection. Such measurement of microbial enzymes might not provide useful information in the testing of specimens obtained from body sites which have a normal microbial flora, such as the throat or gastrointestinal tract. However, the detection of specific microbial enzymes in body sites which are normally sterile, such as blood, cerebrospinal fluid, pleural fluid, and urine obtained by suprapubic aspiration would be indicative of pathologic infection. Misinterpretation of positive blood and body fluid cultures due to contamination of skin flora, a problem with any blood culture system, can be minimized by the testing of multiple specimens from the same patient. This multiple testing would be facilitated by the development of assay systems which can test the small volume of blood obtained by capillary puncture. The ability to test small volumes of blood will be an especially important aid to the diagnosis of systemic infection in infants and small children, from whom it is difficult to obtain sufficient volumes of venous blood for standard blood culture cultivation techniques.

This invention therefore provides an efficient, practical, and rapid diagnostic system for the detection of serious bacterial and fungal infections in mammals, especially in human beings. The availability of such a diagnostic system will lead to the more rapid institution of appropriate antimicrobial chemotherapy and a decrease in the inappropriate usage of antibiotics, thus leading to a decrease in the morbidity and mortality associated with infectious diseases.

DESCRIPTION OF THE PREFERRED EMBODIMENTS

In one major embodiment of this invention, $\beta$-lactamase enzymes (penicillinase, cephalosporinase) [E.C. 3.5.2.6], which are penicillin amido-$\beta$-lactam hydrolases, are assayed. $\beta$-lactamases catalyse the conversion of pencillin compounds to the corresponding pencillinoic acid (penicilloate). $\beta$-lactamases are widely distributed in bacterial organisms but are not found in mammalian cells. The fact that $\beta$-lactamase produced by bacteria is often extruded into the external mileau facilitates the measurement of this enzyme in clinical specimens. Also, while there are a number of different structural types of $\beta$-lactamase, all are capable of catalyzing the above reaction. Thus an assay which could measure the formation of penicillinoic acid from penicillin would be capable of detecting any structural type of $\beta$-lactamase. In order to be useful as a diagnostic test, an assay for $\beta$-lactamase would have to detect small amounts of penicillinoic acid without interference from lipids, proteins and other compounds which are present in clinical specimens.

Preliminary studies revealed that currently available assays for $\beta$-lactamase such as spectrophotometric, and microbiological systems were neither sufficiently sensitive nor specific to be useful as diagnostic tests for microbial infection.

Quantitation of the conversion of penicillin to penicillinoic acid can be achieved by any sufficiently sensitive means of measuring the amount of penicillinoic acid. However, a preferred method of quantitation is using a radioisotape labeled substrate.

An enzyme radioisotope assay (ERIA) was developed for the quantitation of the enzymes assayed in this invention. For $\beta$-lactamase, the ERIA is based on the fact that the conversion of penicillin to penicillinoic acid results in the generation of an extra negatively-charged carboxyl group. Because of this extra negative charge, penicillinoic acid will bind to a positively charged ion-exchange resin such as diethylamino ethyl cellulose. Thus, under optimal conditions of pH and ionic strength, $^{14}C$-penicillinoic acid will bind to a small chromatography column containing positively charged resin, while $^{14}C$-penicillin will pass through the column. After washing the column, the $^{14}C$-penicillinoic acid can be eluted by adding a high molarity buffer such as 2M NaCl, and the radioactivity in the fractions, containing $^{14}C$-penicillin and $^{14}C$-penicillinoic acid, can be measured by scintillation counting. Since this method directly measures penicillinoic acid, it is not affected by interference from extraneous molecules which might be present in clinical specimens.

To perform the assay, the specimen is added to a measured amount of $^{14}C$-penicillin. After a suitable incubation period, the amount of $^{14}C$-penicillinoic acid generated is measured by the above method. The amount of non-enzymatic breakdown is determined by running a control reaction in which an excess of unlabelled penicillin is added. This excess substrate will saturate the $\beta$-lactamase system but will not affect the non-enzymatic breakdown of penicillin. The amount of enzymatic conversion of $^{14}C$-penicillin to $^{14}C$-penicillinoic acid is directly proportional to the amount of $\beta$-lactamase in a specimen. Preliminary experiments revealed that this assay system could be used to detect $\beta$-lactamase producing bacteria such as *Escherichia coli, Staphylococcus aureus,* Klebsiella and Pseudomonas, infecting blood, cerebrospinal fluid, and other body fluids.

Detailed Description of an enzyme radioisotope assay (ERIA) for $\beta$-lactamase There are a number of available enzymatic assays for $\beta$-lactamase. These include iodometric, spectrophotometric and colorimetric assay systems. However, these assays can not detect less than $10^{-4}$ units of $\beta$-lactamase and are thus not sufficiently sensitive to detect $\beta$-lactamase in body fluids of patients infected with $\beta$-lactamase producing organisms. In addition, the results of these conventional assays are non-specifically altered by proteins and lipids present in the specimens. This is especially true in the case of the iodometric assays, which are the most widely used assays for the measurement of small amounts of $\beta$-lactamase. A number of immunological assays for the measurement of $\beta$-lactamase were also investigated. While these were more sensitive than the conventional enzymatic assays and were not altered by serum proteins, it was found that there was insufficient cross-reactivity among bacterial $\beta$-lactamases to allow for the use of a single antigen-antibody system for the detection of $\beta$-lactamase from different organisms. Thus the immunoassays are not applicable to wide-scale diagnostic use.

In order to overcome these problems, this invention affords an enzymatic radioisotopeassay (ERIA) based on the principle that penicillinoic acid, the enzymatic product of the reaction of penicillinase and penicillin G, has increased affinity for a positively charged ion exchange resin such as DEAE-Sephadex. The effect of the spontaneous breakdown of penicillin, which occurs slowly in aqueous solutions, is controlled by performing a reaction in which the specimen is incubated with an excess of unlabelled penicillin, thus saturating the enzyme system but not effecting non-enzymatic hydrolysis.

The procedure utilized in this embodiment is as follows.

1. One part of specimen is incubated with 0.5 to 2 part (preferably about 1 part) of incubation broth (preferably trypticase soy broth) and sufficient radioactive isotope labeled $\beta$-lactamase sensitive antibiotic substrate to afford about 0.1 to 0.5 microcuries ($\mu$Ci) of activity (preferably about 0.3 $\mu$Ci) per 50 $\mu$l of specimen. In additional one part of specimen may be incubated in the same manner, only with an unlabelled antibiotic substrate, utilized as a control against non-enzymatic hydrolysis. In this instance, the amount of unlabeled antibiotic is one part with a concentration of about 4 to 16 mg/ml (preferably about 8 mg/ml).

2. The reaction mixture is then incubated for $\frac{1}{2}$ to 2 hours (preferably about 1 hour) at 27° C. to 40° C. (preferably about 37° C.) with agitation (preferably by means of a shaking water bath).

3. The reaction mixture is then transferred to a disposable column containing a positively charged ion-exchange material which has been equilibrated with a 0.03M buffer to a pH of about 7.2 to 8.0 (preferably a pH of about 7.8). A preferred ion-exchange material is diethylamine ethyl cellulose and a preferred buffer is a tris (hydroxymethyl) aminomethane salt (Tris).

4. The unreacted antibiotic substrate is removed from the column by washing with the same or a similar buffer.

5. The reacted antibiotic substrate is eluted with a suitable buffer, (preferably a 2.0 to 4.0M buffer, most preferably a 2.0M salt buffer).

6. The unreacted and the reacted antibiotic substrates are then quantitated separately, using any suitable apparatus and method for radioactive istopes. Where the unreacted substrate is the preferred $^{14}C$-penicillin and the reacted substrate is $^{14}C$-penicillinoic acid, a scintillation counter is preferred. Where the radioactive label is $^3H$, autoradiography is also useful, but a scintillation counter is preferred.

7. The percent conversion of unreacted substrate to reacted substrate is calculated quite simply using the formula $$\% \text{ Conversion} = \frac{RS}{US + RS} \quad (I)$$

where RS is the activity of the reacted substrate eluted in step 5 and measured in step 6, and US is the unreacted substrate removed in step 4 and measured in step 6.

8. For the purposes of this invention, a specimen is considered to contain $\beta$-lactamase if the percentage conversion is two standard deviations greater than the mean of negative controls and if this percentage conversion is reduced in the unlabeled control to a statistically significant extent.

The useful antibiotics in this invention are those having a $\beta$-lactam ring which are substrates for $\beta$-lactamase, preferably at least one of the group consisting of: benzylpenicillin (penicillin G); phenoxyethyl penicillin (phenethicilin); ampicillin, carbenecillin, and amoxycillin (amoxycillin). Of these, benzylpenicillin is most preferred. $\beta$-lactamase resistant penicillins such as methicillin and oxycillin are obviously not useful in this invention. The radioactive isotopes useful in this invention are any that are capable of labeling the above useful antibiotics, preferably radioactive isotopes of carbon, hydrogen, iodine, nitrogen, or sulfur, most preferably $^{14}C$, $^3H$, or $^{32}S$ and particularly $^{14}C$.

EXAMPLE I

A series of β-lactamase assays were performed according to the above embodiment of this invention, as follows.

MATERIALS AND METHODS

Carbon 14-labeled benzylpenicillin was purchased from Amersham Corporation and was further purified by the following procedure: Fifty microcuries were diluted in 1 ml of 0.03M tris(hydroxymethyl)aminomethane salt (pH 7.8) buffer, and added to a disposable column packed with 1.5 ml of diethylamino ethyl cellulose (a positively charged ion-exhange resin) equilibrated with 0.03M tris(hydrozymethyl)amino-methane salt. The $^{14}$C-benzylpenicillin was eluted with buffer. The fractions containing the $^{14}$C-benzylpenicillin were pooled, lyophilized, and stored at $-20°$ until use. Beta-lactamase, Type II, was obtained from Sigma Chemical Company, St. Louis. As stated by Sigma Chemical Company, this is a crude, lyophilized, powder containing approximately 75% protein, the balance being primarily buffer and zinc salts, which was produced by *Bacillus cereus*. Disposable polyvinyl columns were purchased from Isolab, Inc., Akron, Ohio.

Specimens

Specimens of cerebrospinal fluid, pleural fluid, peritoneal fluid, or blood were collected from patients following established procedures. On receipt, the specimens were either tested immediately for β-lactamase or stored at $-20°$ C. until ERIA testing was performed. Gram stain and cultivation studies were performed following established techniques.

Broth cultures of various bacteria were prepared from clinical isolates by growth in trypticase soy media. The cultures were grown under log-phase conditions and diluted to contain approximately $10^4$ organisms/ml as measured by the turbidity method of McFarland prior to testing for β-lactamase.

β-Lactamase assay

A 50 μl aliquot of test specimen, β-lactamase standard, or negative control was added to a $12\times75$ mm sterile polypropylene tube containing 40 μl of trypticase soy broth. A 10 μl aliquot of purified $^{14}$C-benzylpenicillin containing approximately 0.2 μCi($10^{-4}$M) was then added and the mixture was incubated at 37° C. in a shaking water bath for 30, 60 or 120 minutes. Aliquots of the incubation mixtures were then transferred to 10 cm disposable polypropylene columns packed with 1.5 ml of diethylamino ethyl cellulose equilibrated with 0.03M tris(hydroxymethyl)aminomethane salt buffer (pH 7.8). The conversion from penicillin to penicillinoic acid results in the generation of a new carboxyl group which will result in an increased affinity to a positively charged gel such as diethylamino ethyl cellulose. Thus, unreacted penicillin was washed off the columns with 6 ml of 0.03M tris(hydroxymethyl)aminomethane salt buffer and the penicillnoic acid formed by the action of the β-lactamase was eluted with 2 ml of 2M NaCl. The washing procedure takes approximately 10 minutes to perform.

The radioactivity of the fractions was measured in a liquid scintillation counter. The percentage of penicillin converted to penicillinoic acid was determined for each specimen by the following formula:

$$\% \text{ Conversion} = \left( \frac{CPM \text{ Penoic}}{CPM \text{ Penoic} + CPM \text{ Pen } G} \right) \times 100$$

where CPM Penoic refers to the counts per minute of the penicillinoic acid-containing fraction eluted with 2M NaCl, and CPM Pen G are the counts in the penicillin-containing fraction eluted with tris(hydroxymethyl)aminomethane salt. This method was utilized to allow for the quantitation of enzymatic activity under substrate limiting conditions. Five negative controls, either uninoculated broth cultures or clinical specimens from patients without evidence of bacterial infection, were included in each test run. A dilution of purified β-lactamase or specimen was considered positive if it yielded a percentage conversion which was 2 SD greater than the mean of the percentage conversion of the appropriate negative controls for the same test run. The mean standard error of the negative controls ranged from 0.9 to 1.4% conversion during different test runs.

The percentage conversion of a specimen was expressed in terms of units of β-lactamase by establishing a standard curve with log-fold dilutions of a preparation of purified β-lactamase. One unit of purified β-lactamase is defined as the amount of enzyme which converts 1μ mole of benzylpenicillin to benzylpenicillinoic acid in 1 minute at pH 7.0 and 25° C. Specimens containing more than $10^{-4}$ units were diluted and retested to ensure accurate quantitation.

Other β-lactamase assays

The microiodometric assay was performed as described by Novick [Biochem J 83:236, 1962]. The results were measured at a wavelength of 620 nm utilizing a spectrophotometer. A specimen was considered positive if it yielded an optical density value that was 2 SD less than the mean of the negative controls. Beta-lactamase was also measured utilizing a chromagenic cephalosporin.

RESULTS

Purified β-lactamase

The results of the ERIA testing of log-fold dilutions of purified β-lactamase showed that the ERIA was capable of detecting $10^{-5}$ units at 30 minutes and $10^{-6}$ units at 60 and 120 minutes. In contrast, the microiodometric assay could detect $10^{-4}$ units at 120 minutes and the chromagenic cephalosporin assay only $10^{-2}$ units.

In order to test the effect of possible interfering substances on the assay system, dilutions of purified β-lactamase were added to pools of uninfected serum, cerebrospinal fluid, and penicillin. The body fluids, and benzylpenicillin at concentrations up to 40 μg/ml, did not affect the sensitivity of the ERIA for the measurement of β-lactamase. Benzylpenicillin at a concentration of 400 μg/ml reduced the sensitivity of the assay approximately tenfold. Human serum did result in an increased rate of conversion of benzylpenicillin to penicillinoic acid. However, this conversion did not affect the sensitivity of the assay as defined above.

Broth cultures

Broth cultures containing approximately $10^4$ organisms/ml of 91 different bacterial isolates were tested for β-lactamase by the ERIA and the iodometric methods. Twelve isolates of *Staphylococcus aureus*, eight isolates of *Escherichia coli*, six of *Pseudomonas aeruginosa*, five of *Klebsiella peneumoniae*, three of *Serratia marcescens* and 16 of other gram-negative bacilli (other than *Haemophilus influenzae*) were positive by both methods. Eight isolates of *Streptococcus pneumoniae*, six of group A beta hemolytic streptococcus, four of group B beta hemolytic streptococcus, and four of *Neisseria meningitidis* were negative for β-lactamase by both methods. In addition, 19 strains of *H. influenzae*, group D streptococcus, and *Neisseria gonorrhoeae* were tested for β-lactamase by both methods. The results of β-lactamase testing of these isolates are presented in Table I. Of the eight strains of *H. influenzae* type b tested, two produced greater than $10^{-4}$ units/$10^4$ organisms of β-lactamase and were detected by both methods. However six produced lower levels of β-lactamase, between $10^{-5}$ and $10^{-6}$ units/$10^4$ organisms, which were detectable only by the ERIA. Similarly, one strain of *N. Gonorrhoeae* produced by $3 \times 10^3$ units/$10^4$ organisms of β-lactamase and was positive by both methods. However, the remaining five strains produced less than $10^4$ units and were detected only by ERIA. Four of five isolates of group D streptococcus produced amounts of β-lactamase which were detectable only by the ERIA method.

Clinical specimens

Potential β-lactamase producing organisms were isolated from a total of 52 specimens. The organisms isolated were *Staphylococcus aureus* 11, *S. epidermidis* 5, *Klebsiella pneumoniae* 8, *E. coli* 5, *Pseudomonas aeruginosa* 5, *Serratia* sp. 4, beta hemolytic streptococcus group D 4, *H. influenzae* 6, *N. gonorrhoeae* 2, and unidentified gram-negative bacilli in 2 of these specimens. Eighteen specimens were tested immediately after they were obtained from patients; 34 were tested following storage.

The results of the direct β-lactamase ERIA on these clinical specimens are depicted in Table II. Forty-nine of the 52 infected specimens (94%) were positive by ERIA. The three false-negative specimens contained the following organisms: group D streptococcus (blood), *Serratia* (blood), and *H. influenzae* type b (CSF). On the other hand, gram-stained examinations were positive on none of the 20 blood specimens and 18 of the 32 body fluid specimens.

There were 125 culture-negative specimens available for testing. Beta-lactamase activity was not detected in 123 (98%) of these specimens by ERIA. One of the ERIA positive-culture negative specimens was pleural fluid from a patient with positive blood cultures for *S. aureus*, from whom only sterile pleural fluid was obtained following treatment with nafcillin. The other was a blood specimen from a patient with fever, lobar pneumonia, and leukocytosis, from whom no incriminating organism could be cultured. This patient responded quickly to treatment with antibiotics.

Five of the seven specimens containing *H. influenzae* type b yielded β-lactamase values of less than $10^{-5}$ units, and grew out ampicillin-sensitive organisms. Two of the specimens had β-lactamase values of greater than $10^{-4}$ units, and both of these subsequently grew out *H. influenzae* type b organisms which were resistant to ampicillin by disc and tube dilution sensitivity methods.

TABLE I

β-Lactamase production of broth cultures of bacterial isolates as measured by enzymetric radioisotopic assay (ERIA) and iodometric assay.

| | ERIA | | Iodometric assay | |
|---|---|---|---|---|
| Organism | Units* ($\times 10^{-6}$) | No. positive/No. tested | Units* ($\times 10^{-6}$) | No. positive/No. tested |
| *H. influenzae* | 3,000 | 7/8 | 10,000 | 2/8 |
| | 1,000 | | 1,000 | |
| | 100 | | N# | |
| | 10 | | N | |
| | 10 | | N | |
| | 3 | | N | |
| | 3 | | N | |
| | N | | N | |
| Group D streptococcus | 30 | 4/5 | N | 0/5 |
| | 30 | | N | |
| | 10 | | N | |
| | 10 | | N | |
| | N | | N | |
| *N. gonorrhoeae* | 3,000 | | 3,000 | |
| | 30 | | N | |
| | 30 | | N | |
| | 10 | | N | |
| | 3 | | N | |
| | N | | N | |
| Total | | 5/6 | | 1/6 |
| | | 16/19## | | 3/19## |

*Per $10^4$ organisms.
N = negative (less than 2 SD above uninfected broth). Minimal detectable β-lactamase was ($10^{-6}$) units for the ERIA and ($10^{-4}$) units for the iodometric assay. Values were determined to the nearest half-log amount. In the case of the ERIA, strongly positive specimens were diluted and retested to ensure accurate quantitation.
P < 0.01.

TABLE II

Results of ERIA β-lactamase testing of body fluids.

| | Bacterial infection* | | No bacterial infection* | |
|---|---|---|---|---|
| Site | No. tested | No. positive | No. tested | No. positive |
| CSF | 13 | 12 | 46 | 0 |
| Pleural | 9 | 9 | 27 | 1 |
| Peritoneal | 7 | 7 | 23 | 0 |
| Joint | 3 | 3 | 8 | 0 |
| Blood | 20 | 18 | 21 | 1 |
| Total | 52 | 49 | 125 | 2 |

*Due to β-lactamase-producing organisms.

Seventeen specimens were tested from which non-penicillinase producing organisms such as *S. pneumoniae*, group A and group B beta hemolytic streptococci, and *N. meningitidis* were cultured. None was positive by the β-lactamase ERIA.

DISCUSSION OF EXAMPLE I

In recent years a number of immunologic assays utilizing reagents labeled with radioactive, fluorescent, or enzymatic markers have been developed for the rapid detection of infectious agents in clinical specimens. However, these immunoassays have the disadvantage that each antiserum can interact with only a single or limited number of antigens. These systems are thus not practical for use in situations in which tests must be done for a large number of different organisms.

Many medically important bacteria produce β-lactamase, which is elaborated into the extracellular medium. Although the β-lactamases elaborated by different groups of bacteria vary in their structure, kinetic properties, and substrate specificity, all are capable of breaking the carbon-nitrogen bond of the lactam ring of benzylpenicillin to produce penicillinoic acid. This reaction results in the formation of a new carboxyl group. Because this group is negatively charged, penicillinoic acid, which has two carboxyl groups, will bind with a positively charged ion-exchanged resin to a greater extent than will benzylpenicillin which has only one carboxyl group.

This principle was used to develop an enzymatic radioisotopic assay for β-lactamase. This assay was capable of detecting $10^{-6}$ units of purified β-lactamase, 100-fold more sensitive than detection by the standard β-lactamase techniques. Since the ERIA specifically measures the generation of $^{14}C$-penicillinoic acid from $^{14}C$-penicillin, it should not be affected by the binding of penicillin to serum proteins and antibodies, or by the presence of therapeutic levels of penicillin in the specimen. Although nonenzymatic breakdown of penicillin can occur slowly in body fluids, the confounding effects of this breakdown could be eliminated by the appropriate negative controls consisting of uninfected body fluids. The β-lactamase ERIA thus offers advantages over other, less direct methods of measuring β-lactamase, such as the iodometric assays, which are affected by serum lipids and proteins.

Since the β-lactamase ERIA measures the activity of an enzyme which is not normally found in human body fluids, this assay is potentially more useful for microbial detection than previously described systems which measure the generation of $^{14}CO_2$ from $^{14}C$ glucose as a marker of bacterial contamination. Those systems measure a metabolic pathway which is common to both bacterial and mammalian cells. Clinical specimens containing metabolically active cells such as leukocytes can thus yield false-positive reactions in those systems. In addition, the ERIA is more rapid than $^{14}CO_2$ measurement systems, and does not require specialized equipment.

In addition to detecting the presence of bacteria, the β-lactamase ERIA provides information about the potential usefulness of penicillin therapy; the finding of high levels of β-lactamase in a specimen would suggest that the infection is not caused by an organism, such as pneumococcus, which might be sensitive to low doses of penicillin G. In addition, the quantitation of β-lactamase might provide the physician with information regarding the initial choice of antimicrobial therapy.

Since rapid identification and quantitation of *H. influenzae* type b antigen is available by a number of immunodiagnostic means, it is possible that the results of the β-lactamase ERIA can be combined with these immuno-assays to indicate appropriate initial therapy for *H. influenzae* infection. Nonpenicillin antibotics such as chloramphenicol might be indicated in *H. influenzae* type b infections associated with a high β-lactamase level in body fluid (greater than $10^{-4}$ units/50 μl), whereas ampicillin could be used if low or absent β-lactamase levels were found in the presence of detectable amounts of *H. influenzae* antigen. The value of this approach should be determined in future studies of a large number of *H. influenzae* infections.

Since both nonpathogenic and pathogenic bacteria can produce β-lactamase, the measurement of β-lactamase activity in body fluids which are not normally sterile, such as sputum or stool, would not provide useful information. Similarly, in the case of blood, cerebrospinal fluid, or pleural fluid cultures, the ERIA cannot distinguish true infections from contamination by skin flora. However, this problem is partially mitigated by the fact that small volumes (50 μl) of specimen can be assayed, thus allowing for the testing of multiple samples from an individual patient.

As an important embodiment of this invention, the detection of β-lactamase in body fluids can be utilized to establish the rapid diagnosis of bacterial infection. The efficiency of the ERIA system for the immediate testing of specimens obtained from patients with suspected infectious diseases should be further determined by a study of a larger number of freshly obtained specimens. The successful use of the β-lactamse ERIA for the rapid diagnosis of bacterial infections could markedly improve the medical management of patients with suspected infectious diseases.

Any of the bacteria or fungi specifically mentioned herein, as well as any microbes not specifically mentioned but which generate any of the β-lactamase enzymes, are useful in this particular embodiment of this invention.

In a second major embodiment of this invention, a related but different microbial enzyme assay is afforded. In order to provide for a comprehensive microbial diagnostic system, there is also the need to detect microorganisms which do not normally produce detectable amounts of β-lactamase. These organisms include pneumococci, meningococci, group A streptococci and the medically important fungi. This embodiment utilizes the measurement of a specific microbial enzyme of adenine metabolism, adenine aminohydrolase, as an additional indicator of microbial infection in clinical specimens. This enzyme catalyzes the uptake and deamination of adenine and other purines by bacterial and fungal cells. However, this enzyme is not found in mammalian cells. This enzyme is responsible for the action and specificity of the antifungal agent, 5-fluorocytosine. However, the enzyme is present even in microorganisms resistant to that antibiotic.

Adenine aminohydrolase (adenine deaminase) [EC 3.5.4.2] catalyses the deamination of adenine (aminopurine) to hypoxanthine (hydroxypurine) as well as the deamination of other purines, and is widely distributed in bacterial and fungal organisms but is not found in mammalian cells, which are not capable of directly converting adenine to hypoxanthine. The conversion of adenine to hypoxanthine results in the loss of a purine associated amino radical. This invention provides measuring adenine aminohydrolase by means of an ERIA based on the fact that the 5-amino group of adenine is positively charged in acidic solution. Thus, in acidic solution, $^3$H-adenine, labelled within the purine ring, will bind to a small ion-exchange column containing a negatively charged gel while the reaction product, $^3$H-hypoxanthine, which does not possess the excess positive charge, will pass through the column. Thus, the amount of radioactivity in the acidic solution will be directly proportional to the amount of hypoxanthine formed by the action of adenine aminohydrolase. Non-enzymatic conversion of adenine to hypoxanthine should be minimal since adenine is very stable in solution.

As for other metabolic pathways of adenine, the conversion of adenine to adenosine monophosphate (AMP) by the enzyme adenine amino phosphoribosyltransferase will be blocked by the addition of an excess of AMP, which is a specific inhibitor of that enzyme. The direct conversion of adenine to adenosine should not occur since the enzyme which converts purines to nucleosides, purine nucleoside phosphorylase, does not utilize adenine as a substrate. Similarly, adenosine deaminase, the mammalian enzyme which converts adenosine to inosine, does not utilize the free purine adenine as a substrate.

Thus, the assay for adenine aminohydrolase of this invention is useful as a rapid diagnostic test for microbial infection. The availability of this assay should markedly increase the sensitivity of the adenine permease system since it will allow for the measurement of adenine which is taken up by microbial cells but deaminated and released into the environment in the form of hypoxanthine. Intracellular $^3$H-hypoxanthine will be released by sonication prior to the column chromatography procedure to allow for the determination of the intracellular pool of $^3$H-hypoxanthine. In addition, the ability to measure adenine aminohydrolase will allow for the measurement of cell wall defective and fragmented microorganisms which might not retain adenine. This is especially important for the diagnosis of fungal infections, since intact, viable organisms often cannot be found even in the presence of overwhelming fungal infection.

Preliminary studies indicated that conventional means of detecting adenine aminohydrolase were not sufficiently sensitive or sufficiently specific to provide means for the rapid detection of microbial infection. However, there difficulties were overcome by using the adenine aminohydrolase enzyme according to this invention, which afforded useful microbial assays.

Thus, this embodiment utilizes ion exchange chromatography to measure tritium-labelled hypoxanthine (6 hydroxy-purine) formed from the deamination of tritium-labelled adenine (5 amino-purine). This ion exchange chromatography is based on the fact that, at an acidic pH the amino group of adenine is positively charged and adenine will bind to a positively-charged ion exchange gel. Hypoxanthine, on the other hand, will pass through the negatively-charged gel since it does not have a positive charge under the experimental conditions. Preliminary experiments revealed that adenine and hypoxanthine can, in fact, be separated by this method and that diluted concentrations of bacterial and fungal organisms can be detected in broth cultures (Table III).

TABLE III

ADENINE AMINOHYDROLASE ACTIVITY OF BROTH SPECIMENS OF MICROORGANISMS AND BODY FLUIDS

|  | % conversion of Adenine to Hypoxanthine[#] |
|---|---|
| Microorganisms ($10^4$/50 μl) | |
| C. Albicans | 3.9 |
| C. tropicalis | 4.8 |
| A. fumigatus | 2.3 |
| S. aureus | 5.1 |
| S. pneumoniae | 1.7 |
| S. viridans | 2.5 |
| K. pneumoniae | 4.0 |
| S. newport | 3.8 |
| P. aeruginosa | 5.6 |
| Uninfected Body Fluids | |
| Blood (n = 6) | 0.8* ± .02 |
| CSF (n = 5) | 0.5 ± .03 |
| Pleural fluid (n = 11) | 0.7 ± .03 |

[#] $\frac{\text{CPM passing through column}}{\text{CPM added to column}} \times 100 = \%$ conversion

*Mean ± 2 standard deviations

In using this ion exchange chromatography system to detect microbial growth in clinical specimens, quantitative determinations are performed to determine if the amount of adenine aminohydrolase measured correlates to the clinical course and the response to therapy.

Detailed description of an enzyme radioisotope assay (ERIA) for adenine aminohydrolase The procedure utilized in this embodiment is as follows.

1. One part of specimen is incubated with 0.5 to 2 part (preferably about 1 part) of incubation broth (preferably trypticase soy broth) and sufficient of a radioactive isotope labelled nucleoside with an amine moiety substrate (preferably a purine; more preferably adenine, cytosine, or 5-fluorocytosine; most preferably adenine) to afford about 0.1 to 0.5 microcuries (μCi) of activity (preferably about 0.3 μCi) per 50 μl of specimen. The radioactive isotopes useful in this invention embodiment are any that are capable of labeling the above useful nucleosides, preferably radioactive isotopes of carbon, hydrogen, iodine, bromine, or nitrogen, most preferably $^{14}$C or $^3$H, and particularly $^3$H. An additional one part of specimen may be incubated in the same manner, with the same substrate, only unlabeled, and utilized as a control against non-enzymatic hydrolysis. In this instance, the amount of unlabeled substrate is 1 part with a concentration of about 4 to 16 mg/ml (preferably about 8 mg/ml).

2. The reaction mixture is then incubated for ½ to 2 hours (preferably about 1 hour) at 27° C. to 40° C. (preferably about 37° C.) with agitation (preferably by means of a shaking water bath).

3. The reaction mixture is then transferred to a disposable column containing a negative ion-exchange material which has been equilibrated with a 0.01M buffer to a pH of about 2.4 to 3.0 (preferably a pH of about 2.8). A preferred negative ion exchange material is a cation exchange resin such as poly[sulfopropyl]-polyglycerylene dextran hydrochloride sold under the trademark "SP-Sephadex" by Pharmacia Fine Chemicals, Inc., Piscataway, New Jersey, U.S.A., and a preferred buffer is glycine.

4. The reacted deaminated nucleoside substrate (which is hypoxanthine when the substrate is adenine aminohydrolase; inosine when the substrate is cytosine; and 5-fluorouracil when the substrate is 5-fluorocytosine) formed by the catalytic action of the enzyme is then eluted with a suitable buffer (preferably glycine with the same molarity and pH as above), after which.

5. The unreacted nucleoside substrate is removed from the column by washing with a 0.2 to 4.0M (preferably 2.0M) salt (preferably NaCl) buffer.

6. The unreacted and reacted nucleoside substrates are then quantitated separately, using any suitable apparatus and method for radioactive isotopes. Where the label is $^{14}C$ or $^{3}H$, a scintillation counter is preferred. Where the label is $^{3}H$, autoradiography is also useful.

7. The percent conversion of unreacted substrate to reacted substrate is calculated quite simply using the formula:

$$\% \text{ Conversion} = \frac{RS}{US + RS} \quad (I)$$

where RS is the activity of the reacted substrate eluted in step 4 and measured in step 6, and US is the unreacted substrate removed in step 5 and measured in step 6.

8. For the purposes of this invention, a specimen is considered to contain adenine aminohydrolase if the percentage conversion is two standard deviations greater than the mean of negative controls and if this percentage conversion is reduced in the unlabeled control to a statistically significant extent.

Other Embodiments Within The Scope Of This Invention

The above ERIA systems are devised for use in laboratories with facilities for measuring radioactive isotopes. However, the assays could also be adapted to non-radioactive use by the development of high performance liquid chromatography (HPLC) systems for the measurement of the products of the enzymatic reactions. The utility of the assays would be expanded still further by the development of enzyme immunoassays (EIA) utilizing highly specific reagents for penicillin, adenine and their respective reaction products. These highly specific reagents might be made by the production of monoclonal antibodies in a mouse-hybridoma system. Since EIA's can be performed without sophisticated equipment, the development of these EIA's would make rapid microbial detection systems available to a large number of health care providers.

The availability of the preferred embodiment systems for rapid diagnosis of infection of this invention would be markedly increased if an alternative to radioactive isotopes could be found. Although the radiation hazard of low energy β-emitters such as Carbon-14 or tritium are sufficiently low so that assays which utilize reagents labelled with these isotopes can be safely performed in many laboratories, such assays cannot be used outside of such facilities. In addition, such radioactive reagents cannot be stored in doctors' offices or in patient care areas, even in institutions which have laboratories licensed for radioactive materials. Thus the reactions of an assay system utilizing clinical specimens and radioactive reagents cannot be initiated until the specimen is brought to a central laboratory facility. In addition, the avoidance of radioactive reagents would markedly decrease the cost of the assay systems.

Also within the scope of this invention are diagnostic kits for performing the disclosed microbial assays. Such kits would comprise a suitable substrate for a microbe generated foreign enzyme resulting from a microbial infection, optionally together with a suitable incubation medium, both of which may be contained in a suitable disposable incubation vessel.

The body fluid specimen to be tested would be added to the incubation vessel in accordance with the teachings of this invention. The kits would also provide a second vessel containing a suitable ion-exchange material, bound to the walls of the vessel or to a suitable filter material within the vessel. A preferred second vessel would be a disposable chromatography column. After incubation in the incubation vessel and buffering, etc., according to this invention, the incubated substrate/specimen mixture would be charged to the second vessel so that the reacted and unreacted substrates can be separated and quantitated in accordance with this invention. The various substrates, incubation media, buffers, and ion-exchange materials afforded in the kit would be those disclosed as suitable elsewhere in this specification.

I claim:

1. A method of detecting a microbial infection in a mammal by measuring for the presence of beta-lactamase enzymes (E.C. 3.5.2.6) generated by the infecting microbes comprising:
   (a) combining an internal body fluid sample taken from the mammal suspected of having a microbial infection with a penicillin substrate having a beta-lactam ring capable of being hydrolyzed by beta-lactamase enzymes under conditions sitable for beta-lactamase activity, wherein said substrate is $^{14}C$-benzylpenicillin;
   (b) determining the presence of beta-lactamase enzyme in said sample by quantitating hydrolysis of said substrate by said enzyme using an ion exchange column to which the cleaved substrate binds; and
   (c) comparing under similar conditions the results in step (b) with a normal predetermined standard for an uninfected mammal of the same species;
wherein appreciably greater amount of hydrolysis of said substrate in the sample as compared to the normal standard is indicative of a microbial infection.

2. The method of claim 1 wherein the assay is qualitative and indicates only the presence or absence of microbial infection.

3. The method of claim 1 wherein te assay is quantitative and indicates the degree of microbial infection, if present.

4. The method of claim 1 wherein the mammal is a human being.

5. The method of claim 1 wherein the body fluid is selected from the group consisting of blood, cerebrospinal fluid, pleural fluid, and urine obtained by suprapubic aspiration.

6. The method of claim 1 wherein the body fluid is blood and a plurality of specimens from the mammal suspected of infection are tested.

7. The method of claim 1 wherein the substrate is hydrolytically cleaved by the enzyme to yield a labeled negatively-charged portion; a positively-charged ion-exchange material is provided; and the assay is effected by loading the ion exchange material with the hydrolyzed sample so that the negatively charged portion is retained by the ion exchange material, then measuring the amount of labeled negatively-charged portion adhering to the positively-charged ion-exchange material by eluting the same from the ion-exchange material and the amount of unreacted substrate passing through the ion exchange material.

8. The method of claim 7 wherein the body fluid sample is mixed with an incubation broth and at least one substrate;

the reaction mixture is then incubated for about 0.5 to 2 hours at about 27° C. to 40° C. with agitation to effect the hydrolytic cleavage;

the reaction mixture is then transferred to a column containing a positive ion-exchange material equilibrated to a pH of about 7.2 to 8.0, said column retaining the negatively charged portion of said substrate;

unreacted substrate is removed from the column by washing with a buffer;

retained substrate is then eluted with a buffer;

the unreacted and the reacted substrates are then quantitated separately using any suitable method;

and the percent conversion of unreacted substrate to reacted substrate is calculated.

9. The method of claim 8 wherein the $^{14}$C-benzylpenicillin, is added to the specimen in an amount sufficient to afford about 0.1 to 0.5 microcuries of activity per 50 microliters of specimen, as the result of which the reacted substrate is $^{14}$C-penicillinoic acid.

10. The method of claim 9 wherein the quantitation is by measurement of radioactivity with a scintillation counter.

11. The method of claim 9 wherein the ion-exchange material is diethylamino ethyl cellulose.

12. A diagnostic assay kit for detecting a microbial infection in a mammal by measuring for the presence of beta-lactamase enzymes (E.C. 3.5.2.6) generated by the infecting microbes comprising:

an incubation vessel containing a penicillin substrate in an incubation medium capable of reacting with said enzyme when a body fluid specimen from said mammal is added to the incubation vessel;

an assay vessel containing an ion exchange material capable of separating reacted and unreacted substrate when content of said incubation vessel is charged to said assay vessel; and means for comparing the results from the assay vessel with a normal standard sample obtained from an uninfected mammal of the same species.

13. The diagnostic assay kit of claim 12 wherein the substrate is selected from the group consisting of: benzylpenicillin, phenoxyethyl pencillin, ampicillin, carbenecillin, and amoxicillin; and wherein the marking label is selected from the group consisting of: radioactive isotope label, a colorimetric label, a fluorometric label, an electron spin resonance label, and a chemiluminescent label.

14. The diagnostic assay kit of claim 13 wherein said substrate has of the marking label a radioactive isotope of: carbon, hydrogen, iodine, nitrogen, or sulfur.

15. The diagnostic assay kit of claim 14 wherein the marking label is $^{14}$C, $^3$H, or $^{35}$S.

16. The diagnistic assay kit of claim 12 wherein the substrate is $^{14}$C-benzylpenicillin.

17. The diagnostic assay kit of claim 13 wherein the substrate is one which is cleaved to yield a labeled negatively charged portion and the ion exchange material is positively charged.

18. The diagnostic assay kit of claim 17 wherein the ion exchange material is ethylamino ethyl cellulose.

19. The diagnostic assay kit of claim 18 wherein the ion exchange material is in chromatography column containing said material.

20. The diagnostic assay kit of claim 13 further containing an incubation broth for the body fluid specimen.

21. The diagnostic assay kit of claim 20 wherein the incubation broth is trypticase soy broth.

22. The diagnostic assay kit of claim 12 comprising:

a substrate consisting essentially of $^{14}$C-benzylpenicillin, a positively charged ion exchange material afforded in a disposable chromatography column, an incubation broth for the body fluid specimen, at least one buffer for eluting reacted or unreacted substrate from said column, and a normal standard for the mammalian species of the tested mammal.

* * * * *